United States Patent [19]
de la Rama et al.

[11] Patent Number: 6,029,091
[45] Date of Patent: Feb. 22, 2000

[54] CATHETER SYSTEM HAVING LATTICE ELECTRODES

[75] Inventors: Alan de la Rama, Cerritos, Calif.; Nadir Saoudi, Rouen, France

[73] Assignee: Irvine Biomedical, Inc., Irvine, Calif.

[21] Appl. No.: 09/112,937

[22] Filed: Jul. 9, 1998

[51] Int. Cl.[7] ...................................................... A61N 1/05
[52] U.S. Cl. ........................ 607/102; 607/101; 607/122; 607/154; 607/148; 607/99; 606/32; 600/374; 600/393
[58] Field of Search ...................... 607/96, 98, 99–102, 607/113, 115, 116, 117, 119, 122, 148, 149, 154; 606/27–33, 41, 42, 129; 600/372–374, 393, 549, 585, 381; 604/171

[56] References Cited

U.S. PATENT DOCUMENTS

| | | | |
|---|---|---|---|
| 5,441,483 | 8/1995 | Avitall | 604/95 |
| 5,540,681 | 7/1996 | Strul et al. | 607/102 |
| 5,702,438 | 12/1997 | Avitall | 607/122 |
| 5,743,903 | 4/1998 | Stern et al. | 607/102 |
| 5,769,880 | 6/1998 | Truckai et al. | 607/101 |

*Primary Examiner*—Kennedy J. Schaetzle

[57] ABSTRACT

A catheter system comprising a delivery catheter and an inner catheter, wherein the inner catheter is deployable and has a plurality of electrodes on the lattices of a trellis fixture. During a deployed state, the trellis fixture is fully extended to have a series of electrodes on a two-dimensional plane for mapping and/or ablation purposes.

5 Claims, 8 Drawing Sheets

CATHETER SYSTEM HAVING LATTICE ELECTRODES

FIELD OF THE INVENTION

The present invention generally relates to improved constructions for a catheter system. More particularly, this invention relates to catheters and methods for mapping and ablating cardiac tissues via a catheter system having a plurality of electrodes mounted on lattices of a retractable trellis fixture at its tip section.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias, which are frequently caused by the presence of an "arrhythmogenic site" or "accessory atrioventricular pathway" close to the inner surface of the chambers of a heart. The heart includes a number of normal pathways, which are responsible for the propagation of electrical signals from the upper to lower chambers necessary for performing normal systole and diastole functions. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols, which have been proven to be highly effective in tachycardia treatment while exposing a patient to minimal side effects and risks. RF catheter ablation is generally performed after conducting an initial mapping study where the locations of the arrhythmogenic site and/or accessory pathway are determined. After a mapping study, an ablation catheter is usually introduced to the target heart chamber and is manipulated so that the ablations tip electrode lies exactly at the target tissue site. RF energy or other suitable energy is then applied through the electrode to the cardiac tissue in order to ablate the tissue of arrhythmogenic site or the accessory pathway. By successfully destroying that tissue, the abnormal signal patterns responsible for the tachycardia may be eliminated.

The tip section of a catheter is referred to herein as the portion of that catheter shaft containing at least one electrode. In one embodiment, a catheter utilized in the endocardial mapping and/or RF ablation is inserted into a major vein or artery, usually in the neck or groin area. The catheter is then guided into an appropriate chamber of the heart by appropriate manipulation through the vein or artery. The tip of a catheter must be maneuverable by a physician from the proximal end of the catheter, so that the electrode means at the tip section can be positioned against the tissue site to be mapped or ablated. The catheter must have a great deal of flexibility in order to follow the pathway of major blood vessels into the heart. It must permit user manipulation of the tip even when the catheter body is in a curved and/or twisted configuration.

The tip section of a conventional electrophysiology catheter that is deflectable usually contains a plurality of electrodes in series. To accurately locate the electrodes inside a heart is not an easy task. The electrodes in series, such as those on a conventional tubular catheter or a loop catheter, can only provide signals information on a one-dimensional basis. The basket type catheter usually has the electrodes arranged in a contour or basket manner. The exact relative location of each electrode in a basket type catheter is distorted because of the effect of its curvature, especially when one side of the basket is compressed against the endocardial wall.

Therefore, there is an urgent clinical need to have a plurality of electrodes in a relatively flat plane so that the signal obtained from each electrode can be correlated and mapped accurately for future ablation operations. A plurality of electrodes on the lattices of a trellis fixture can provide the endocardial signals in a series of precise pre-determined relative coordinates for mapping assessment.

SUMMARY OF THE INVENTION

In general, it is an object of the present invention to provide an improved catheter for intimate contact with the target tissues. It is another object of the invention to provide a catheter system with a tip section having a plurality of electrodes in a plane. It is another object of the invention to provide a catheter having a plurality of electrodes to be used in effectively mapping the arrhythmogenic regions of a patient and/or subsequent ablation. It is still another object of the present invention to provide a catheter with a retractable trellis fixture mounted on the tip section of the catheter, wherein the trellis fixture comprises a plurality of lattices and a plurality of electrodes mounted on the lattices of the trellis fixture.

In one embodiment, a catheter system comprises a delivery catheter having a distal section, distal and proximal ends, and at least one lumen extending therebetween. A handle is attached to the proximal end of the delivery catheter, wherein the handle has a cavity. An inner catheter is located within one of the at least one lumen of the delivery catheter, wherein the inner catheter has a tip section, a distal end, a proximal end, and a lumen extending therebetween. An electrode deployment means is located at the handle, wherein the electrode deployment means is secured to the proximal end of the inner catheter. The electrode deployment means comprises a non-deployed state for the tip section when the tip section is positioned within the delivery catheter, and further comprising a deployed state for the tip section when the tip section is advanced out of the distal end of the delivery catheter. A retractable trellis fixture mounted on the tip section, wherein the retractable trellis fixture comprises a plurality of lattices and a plurality of electrodes mounted on the lattices of the trellis fixture.

The "trellis fixture" of the present invention refers to a structure having a first plurality of lattices positioned essentially perpendicular to a second plurality of support lattices, wherein all lattices are connected in a way so that it forms a trellis-like structure. The trellis-like structure has a central member that is perpendicular to the first plurality of lattices, and is securable to the tip section of the inner catheter. The above description is in a fully extended state for the preformed trellis fixture. The lattices of the trellis fixture may be constructed of plastic or metallic materials, wherein the surface of the lattices is non-conductive. In one embodiment, the lattice has a lumen, which lumen is connected to each other and to the central member of the trellis fixture. In another embodiment, the trellis fixture has a retracted state when the tip section, including the trellis fixture, is retracted to within the lumen of the delivery catheter. Under this retracted state, the first plurality of lattices is bendable so that they can be retracted to within the delivery catheter.

The delivery catheter has an electrode deployment means. The electrode deployment means includes a deployed state and non-deployed state. The deployment operation can be controlled by a push-pull plunger or a rotating ring to advance and withdraw the inner catheter relative to the delivery catheter. During the deployed state, the inner catheter is advanced out of the distal end of the delivery catheter. The trellis fixture is fully extended because of its preformed shape. During the non-deployed state, portion of the lattices is bendable to fit inside the lumen of the delivery catheter axially. The degree of deployment is controlled by the pushing action of a push-pull mechanism on the handle and is generally fully deployed when the catheter system is ready for mapping or ablation operations inside the chamber of the heart. In another particular embodiment, the material for the electrodes may consist of conductive metals such as platinum, iridium, gold, silver, stainless steel, Nitinol, or an alloy of their mixture.

In an alternate embodiment, the electrode is a band or coil electrode, which has a sharp needle-like end on its surface. In general, the sharp end has a conductive surface for electrical conductivity and/or RF energy delivery while the remaining portion of said electrodes may have insulative body or insulative surface coating. The electrodes of this invention are insulated from the lattice materials.

An insulated conducting wire which is secured to each electrode passes through the lumen of the lattices, the lumen of the central member of the trellis, and the interior cavity of the handle and is thereafter secured to a contact pin of the connector at the proximal end of the handle. From there, the conducting wire is connected to an external RF generator for delivering RF energy or to an EKG monitor for mapping studies. Since the relative location of each electrode is pre-determined, the electrophysiology mapping becomes precise and accurate.

The catheter system may further comprise a steering mechanism at the handle for controlling the deflection of the distal section of the delivery catheter. In one embodiment, said steering mechanism is to assist the positioning of said deployed electrodes to be at the close proximity of the target tissue. Usually a rotating ring or a secondary push-pull plunger on the handle is employed as an integral part of the steering mechanism. One end of the steering wire is secured at certain point of the tip section of said delivery catheter, which is within the lumen of said delivery catheter. The other end of the steering wire is attached to the steering mechanism at the handle. The steering mechanism on a steerable catheter or device is well known to those who are skilled in the art.

In an additional embodiment, the catheter system further comprises at least one temperature sensor and close-loop temperature control mechanism for the electrode having a temperature sensor at the tissue contact site of the electrodes. The location of the temperature sensor is preferably in the proximity of the electrode. One end of the insulated temperature sensing wires is secured to the temperature sensor while the other end is connected to an external temperature control mechanism. A thermocouple or thermister type temperature sensor and control mechanism on a catheter system is well known to those who are skilled in the art.

The delivery catheter having a tip section under a non-deployed state is inserted into the body through a cut at the artery or vein. After the catheter approaches the target tissue inside one chamber of the heart, the tip section, including the trellis fixture, is deployed by being pushed out of the delivery catheter from a push-pull mechanism at the handle. Once positioned, the plurality of electrodes in an essentially perpendicular array in a plane contacts the target tissue intimately for mapping and/or ablation operations. RF energy can be delivered for ablation purpose. As a result of the trellis-type electrode arrangement, a whole area can be mapped simultaneously, particularly effective for atrial fibrillation and atrial flutter indications.

The system and methods of the present invention have several significant advantages over known catheter apparatus and methods. In particular, a set of two-dimensional electrodes of the catheter system of this invention results in a more accurate and more intimate means for mapping and/or ablation capabilities.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
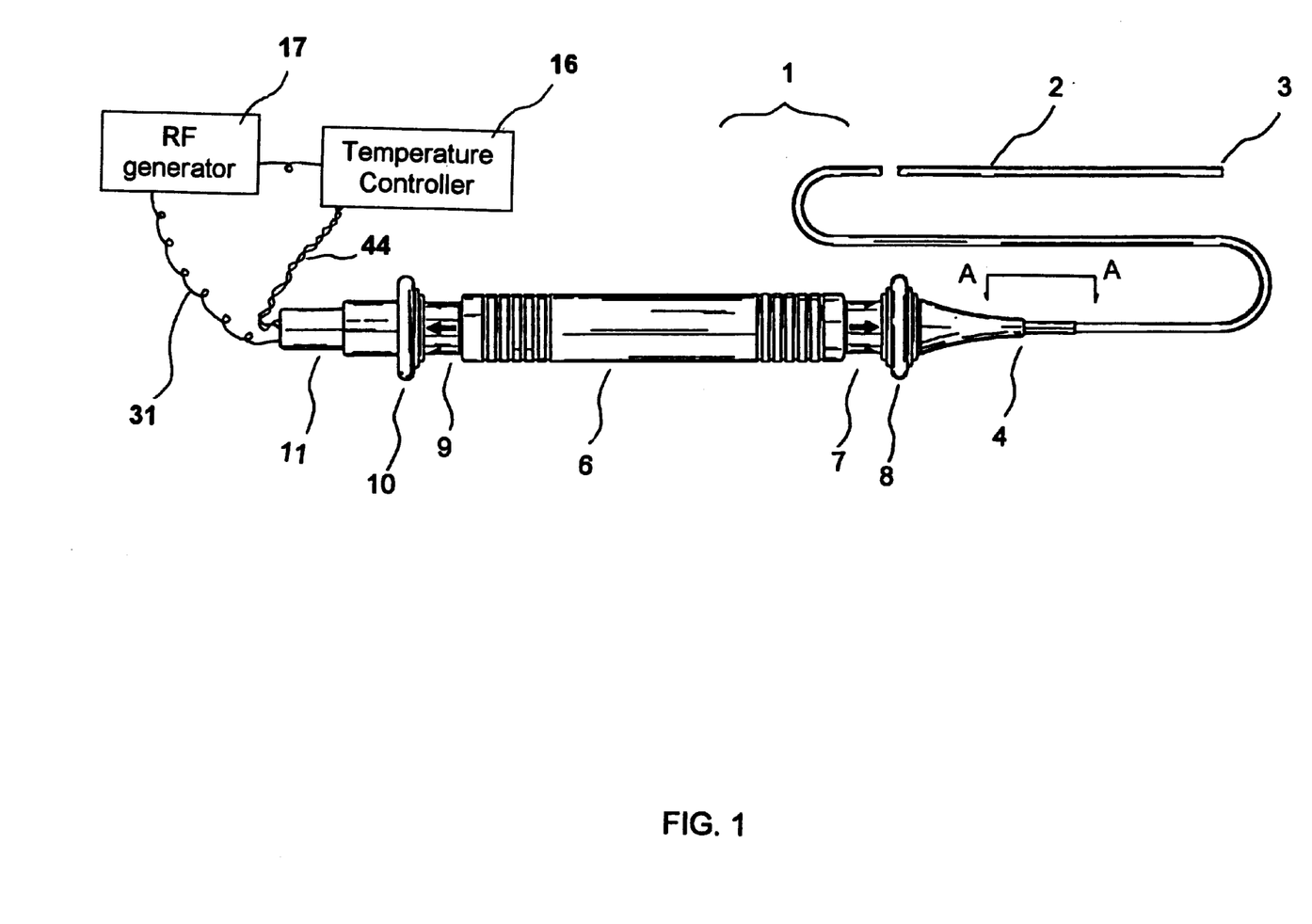
FIG. 1 is an overall view of a catheter system having trellis-like electrodes at its distal tip section constructed in accordance with the principles of the present invention.
Figure 1A:
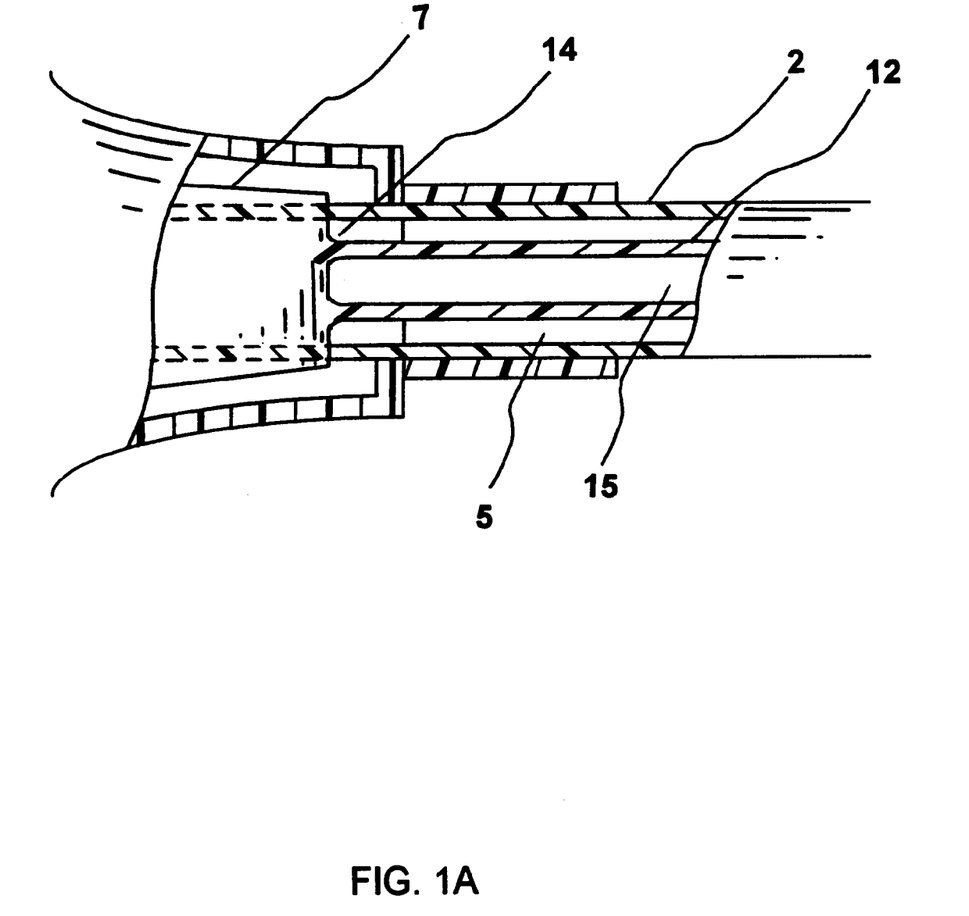
FIG. 1A is a cross-sectional view of the section A—A of FIG. 1.

A catheter system constructed in accordance with the principles of the present invention comprises a delivery catheter and a deployable inner catheter having a trellis fixture and a plurality of electrodes mounted on the lattices of the trellis fixture. FIG. 1 shows an overall view of the catheter system 1 having a delivery catheter 2 with a distal end 3, a proximal end 4, and at least one lumen 5. A handle 6 is attached to the proximal end 4 of said delivery catheter 2. An inner catheter 12 has a distal end 13, a proximal end 14, and a lumen 15 is located within the lumen 5 of the delivery catheter 2. The proximal end 14 of the inner catheter is attached to a push-pull mechanism 7 on the handle 6. A pushing plunger 8 at the push-pull mechanism 7 is used to control the degree of pushing action for the deployment of the inner catheter 12. A steering mechanism 9 and a connector 11 are located on the handle 6.

Figure 2:
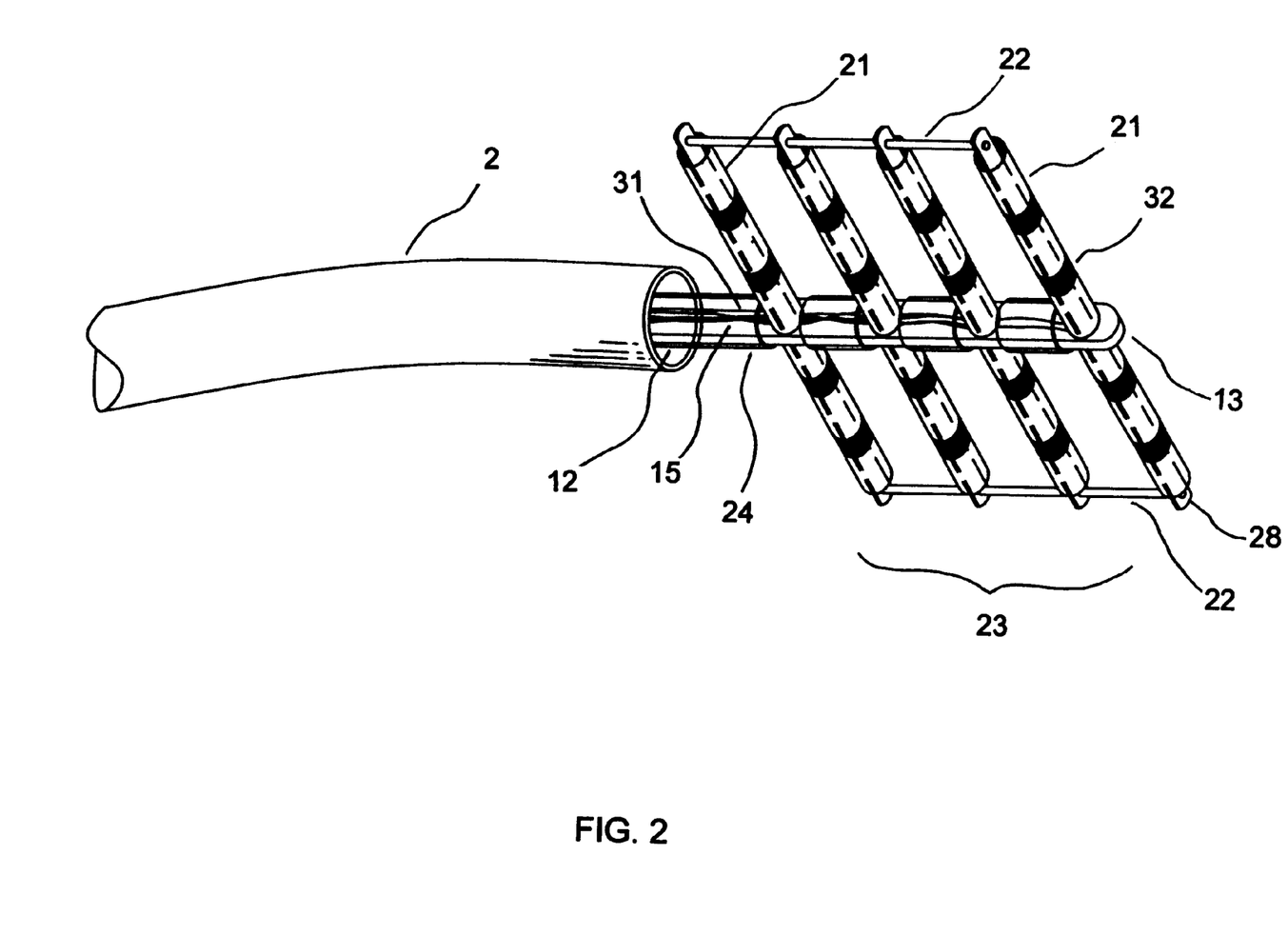
FIG. 2 is a simulated view of the distal section of the catheter system under a fully deployed state.

FIG. 2 shows a simulated view of the distal section of the catheter system under a fully deployed state. The inner catheter 12 comprises a first plurality of lattices 21 positioned essentially perpendicular to a second plurality of support lattices 22, wherein all lattices are connected in a manner so that it forms a trellis-like structure 23. The trellis-like structure has a central member 24 that is perpendicular to the first plurality of lattices 21, and is secured to the tip section of the inner catheter 12.

An insulated conducting wire 31, which is secured to each electrode 32, passes through the lumen 25 of the lattices 21, the lumen 15 of the central member 24 of the trellis 23, and the interior cavity of the handle 6 and is thereafter secured to a contact pin of the connector 11 at the proximal end of the handle 6. From there, the conducting wire 31 is connected to an external RF generator for RF energy delivery or to an EKG monitor for mapping studies. Since the relative location of each electrode 32 is pre-determined, the electrophysiology mapping becomes precise and accurate. The electrode 32 can be either a band electrode, ring electrode, coil electrode 32A, mesh electrode 32B, or other proper form.

Figure 3:
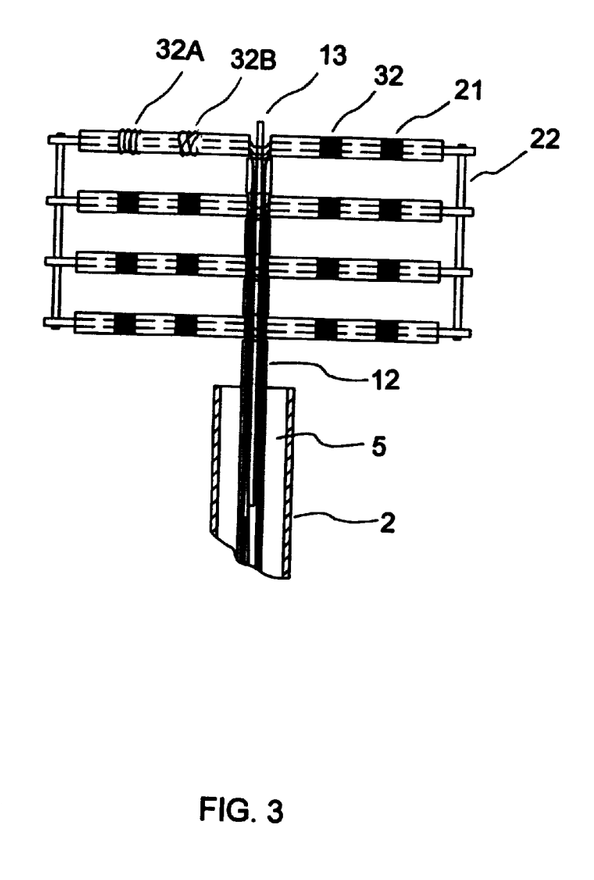
FIG. 3 is a cross-sectional view of the distal section of the catheter system of FIG. 2.
Figure 4:
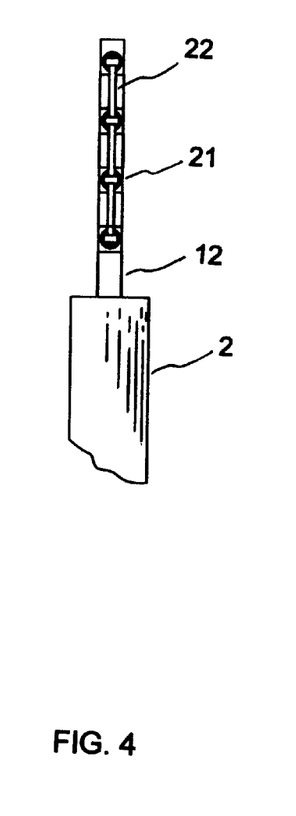
FIG. 4 is a transverse view of the distal section of FIG. 3.

FIG. 3 shows a cross-sectional view of the distal section of the catheter system 1. The delivery catheter 2 has a distal end 3 and a lumen 5, wherein the inner catheter 12 is located within the lumen of the delivery catheter 2. A plurality of lattices 21 and support lattices 22 constitutes part of the trellis fixture 23. FIG. 4 shows a transverse view of the trellis fixture 23, wherein the lattices and the support lattices are connected together.

Figure 5:
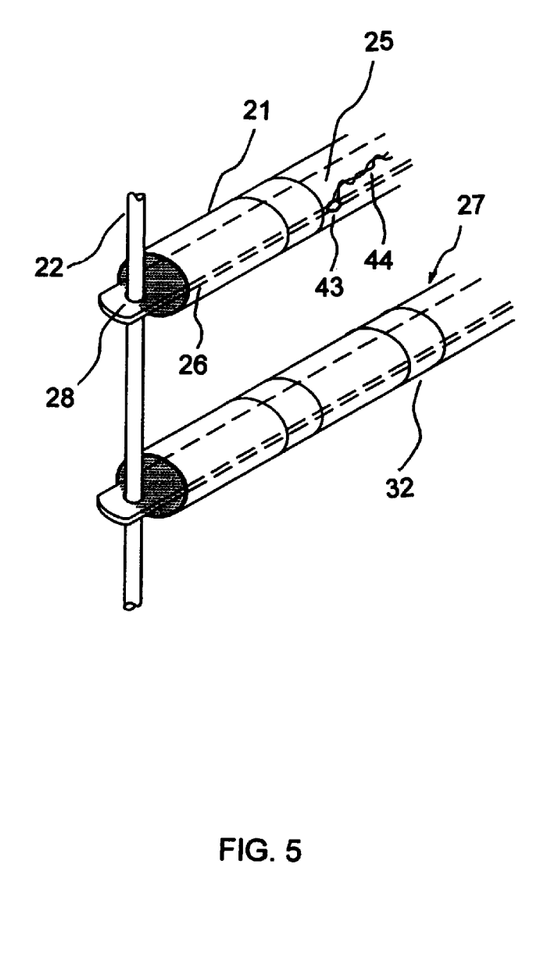
FIG. 5 is a close-up view of a connecting structure for the lattices of the trellis fixture.

FIG. 5 shows a close-up view of the connecting structure for the lattices 21 and the support lattices 22 of the trellis fixture 23. The connecting point 28 between a lattice 21 and a support lattice 22 is loosely, but securely, connected. This loose connector 28 is to facilitate the smooth transition for the trellis fixture from the deployed state to a non-deployed state, and vice versa. In one embodiment the lattice 21 is constructed of an elongate tubular element 27 with a flat wire 26 located within the lumen 25 of the lattice.

Figure 6:
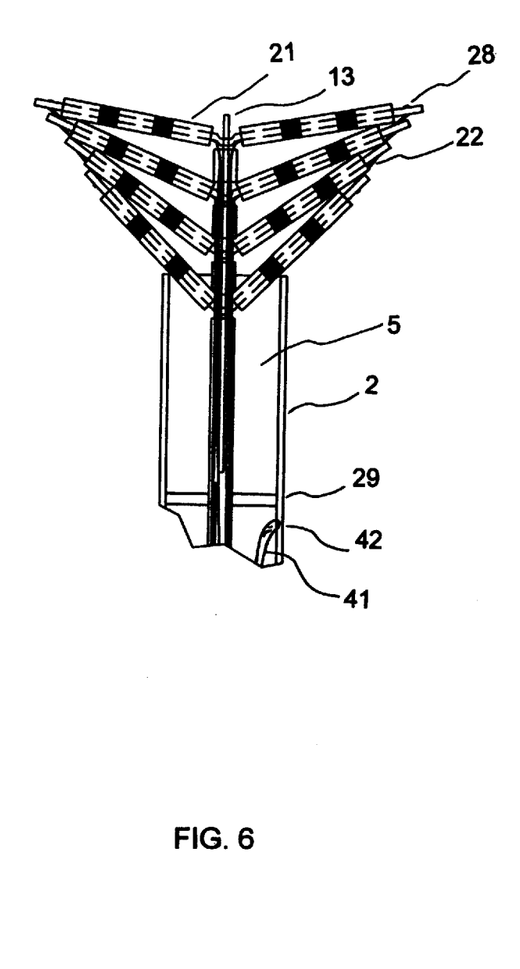
FIG. 6 is a cross-sectional view of the distal section of the catheter system during a partially deployed state.
Figure 7:
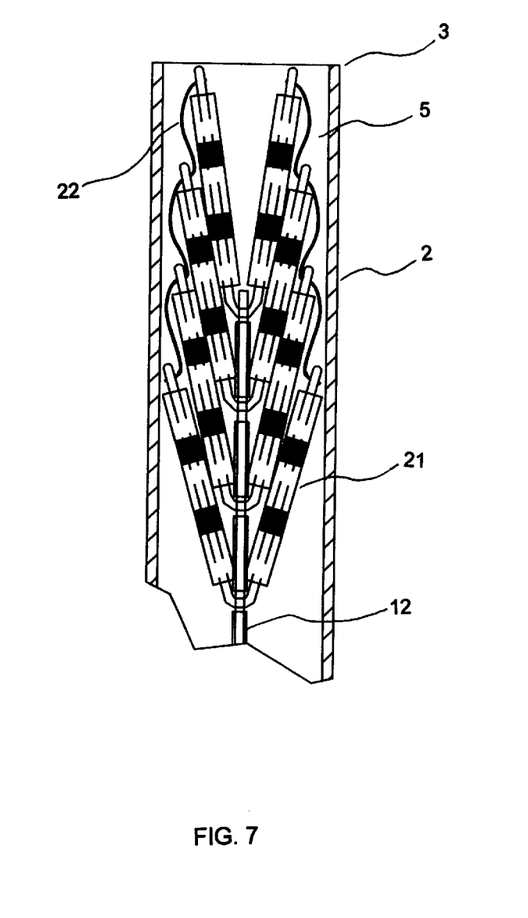
FIG. 7 is a cross-sectional view of the distal section of the catheter system during a non-deployed state.

FIG. 6 shows a cross-sectional view of the distal section of the catheter system 1 during the partially deployed state. The lattice 21 at the most proximal end is bendable to fit into the lumen 5 of the delivery catheter 2 at the initial stage of the retraction operation. The support lattice 22 serves to hold the lattice 21 in the same plane, but not to obstruct the retraction activity because the connecting point 28 is only loosely and securely connected between the lattice 21 and the support lattice 22. At the end of the fully retracted state or the non-deployed, all elements of the inner catheter 12 are inside the lumen 5 of the delivery catheter 2. The retraction operation is controlled by a push-pull mechanism 7 and optionally a push-pull plunger 8 of the catheter system.

To prevent blood or body fluid from backflowing into the proximal end of the lumen of the delivery catheter 2, a silicone type check valve 29 is installed at certain opening point of the lumen 5 of the delivery catheter 2.

In a further embodiment, the catheter system may further comprise a steering mechanism 9 at the handle 6 for controlling the deflection of the distal section of the delivery catheter 2 (FIG. 1). The steering plunger 10 of the steering mechanism 9 at the handle 6 is used to control the degree of deflection of the distal end 3 of the delivery catheter 2. One end of the steering wire 41 is secured at certain distal point 42 of said delivery catheter 2 while the other end is secured to the steering mechanism 9 at the handle 6. The steering mechanism on a steerable catheter is well known to those who are skilled in the art.

In an additional embodiment, the catheter system further comprises a temperature sensor 43 and a close-loop temperature controller for the electrode having a temperature sensor at the tissue contact sites. Temperature sensing wires 44 along with a thermocouple or thermister means is provided to transmit the temperature data from the tissue contact site to an external temperature measuring and control apparatus 16. An algorithm is equipped for the ablation system so that a close-loop temperature control is effective and the temperature data is relayed to an external RF generator 17 for controlled energy delivery.

From the foregoing, it should now be appreciated that an improved catheter system comprising lattice electrodes in a trellis fixture has been disclosed for tissue mapping and/or ablation procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
   a delivery catheter having a distal section, distal and proximal ends, and at least one lumen extending therebetween;
   a handle attached to the proximal end of the delivery catheter, wherein the handle has a cavity;
   an inner catheter located within one lumen of the delivery catheter, wherein the inner catheter has, a distal end, a tip section on the distal end, a proximal end, and a lumen extending therebetween;
   an electrode deployment means located at the handle, wherein the electrode deployment means is secured to the proximal end of the inner catheter, the electrode deployment means comprising a non-deployed state for the tip section when the tip section is positioned in the delivery catheter, and further comprising a deployed state for the tip section when the tip section is advanced out of the distal end of the delivery catheter;
   a retractable trellis fixture mounted on the tip section, wherein the retractable trellis fixture comprises a first plurality of lattices positioned essentially perpendicular to a second plurality of support lattices, wherein a plurality of electrodes is mounted on the first plurality of lattices of the trellis fixture, and wherein all lattices are connected in a way so that it forms a trellis structure; and
   a central member secured to the tip section of the inner catheter, wherein the central member is perpendicular to the first plurality of lattices.

2. The catheter system as in claim 1 further comprising a steering mechanism at the handle for controlling deflection of a distal tip section of the catheter system.

3. The catheter system of claim 2, wherein the retractable trellis fixture has a preformed shape when the electrode deployment means is at its deployed state.

4. The catheter system as in claim 1 further comprising a RF generator for generating RF energy, and a plurality of electrical conductors, wherein the RF energy is delivered to the plurality of electrodes through the plurality of electrical conductors.

5. The catheter system as in claim 4 further comprising a temperature sensor mounted at the tip section of the inner catheter and a closed-loop temperature control mechanism connected to the RF generator of the catheter system, wherein temperature sensed by the temperature sensor is relayed to the closed-loop temperature control mechanism for controlling RF energy delivered to the plurality of electrodes.

* * * * *